United States Patent [19]

Eek

[11] Patent Number: 5,741,956
[45] Date of Patent: Apr. 21, 1998

[54] PROCESS FOR THE PREPARATION OF PENTAERYTHRITOL

[75] Inventor: Lluis Eek, Barcelona, Spain

[73] Assignee: Patentes y Novedades, Barcelona, Spain

[21] Appl. No.: 756,340

[22] Filed: Nov. 26, 1996

[30] Foreign Application Priority Data

May 22, 1996 [ES] Spain .................................... 9601129

[51] Int. Cl.$^6$ .................................................. C07C 29/20
[52] U.S. Cl. ............................................................ 568/853
[58] Field of Search .................................... 568/844, 853, 568/854

[56] References Cited

U.S. PATENT DOCUMENTS

| | | |
|---|---|---|
| 2,790,836 | 4/1957 | Mitchell et al. . |
| 2,978,514 | 4/1961 | Poynton . |
| 3,975,450 | 8/1976 | Palmer et al. . |
| 4,083,931 | 4/1978 | Lee . |
| 4,105,575 | 8/1978 | Eckler . |
| 4,277,620 | 7/1981 | Gupton et al. . |
| 4,328,366 | 5/1982 | Winslow, Jr. et al. . |
| 4,612,389 | 9/1986 | Gupton et al. . |

FOREIGN PATENT DOCUMENTS

| | | |
|---|---|---|
| 626804 | 1/1962 | Belgium . |
| 261843 | 7/1988 | Czechoslovakia . |
| 1 162 824 | 1/1962 | Germany . |
| 1 910 057 | 3/1968 | Germany . |
| 799182 | 1/1957 | United Kingdom . |
| 958654 | 12/1959 | United Kingdom . |

*Primary Examiner*—Gary Geist
*Assistant Examiner*—Karl Puttlitz
*Attorney, Agent, or Firm*—Staas & Halsey

[57] ABSTRACT

A process for the preparation of pentaerythritol, comprising reacting formaldehyde, acetaldehyde and sodium hydroxide and acidification with formic acid. These steps take place in a reactor with supplies of formaldehyde, sodium hydroxide, acetaldehyde and formic acid and at the end the solution formed is evacuated to a buffer tank of larger capacity than the reactor. In the reactor new reactions and acidifications are successively reinitiated by new supplies. In the first place a formaldehyde solution is added, followed by simultaneous but separate additions of sodium hydroxide solution and acetaldehyde, forming a reaction mixture in such a way that the flowrates of the solutions vary with the time and that the temperature at which the reactions are conducted also varies with the time. The outflow from the buffer tank is constant and continuous.

11 Claims, No Drawings

PROCESS FOR THE PREPARATION OF PENTAERYTHRITOL

FIELD OF THE INVENTION

This invention concerns a process for the preparation of pentaerythritol, comprising the initial steps of: [a] reacting formaldehyde with acetaldehyde, to give pentaerythritose; and subsequent reaction of the pentaerythritose with formaldehyde and sodium hydroxide, to give a solution containing pentaerythritol; and [b] acidification of said pentaerythritol-containing solution with formic acid; said steps [a] and [b] being conducted in a reactor, with the supply of formaldehyde ($CH_2O$), sodium hydroxide (NaOH), acetaldehyde (AcH) and formic acid (HCOOH) and at the end of said steps the formed pentaerythritol-containing solution being drained to a buffer tank of a capacity greater than that of the reactor, new reactions and a new acidification operation being successively reinitiated in said reactor by fresh supplies.

The manufacture of pentaerythritol has been known for many years and, as stated in the above paragraph, is based on the reaction of formaldehyde with acetaldehyde in a basic medium. The formate corresponding to the base used is obtained in the process. As alkaline agents, basically used are calcium hydroxide and sodium hydroxide, the latter being the one used in the present process.

PRIOR ART REFERENCE

A number of side reactions giving rise to many by-products occur in the pentaerythritol manufacturing process. Thus, in the basic medium used, various pentaerythritol formals are formed, mainly the cyclic monoformal (known as CMF) and the linear monoformal (known as PMF), the amount thereof being larger the greater is the excess of formaldehyde relative to the acetaldehyde used in the reaction. Also formed are dipentaerythritol, tripentaerythritol and polipentaerythritols in general, the proportions of which in the reaction liquor are increased if the proportion of formaldehyde added relative to the acetaldehyde is reduced. Also, in an alkaline medium, the formaldehyde autocondenses forming sugar type polyhydroxylated compounds, generically known as formoses. The acetaldehyde also produces aldol type condensation products which may react both with themselves and with the other compounds in the reaction medium.

All these reactions show the complexity of the process and explain the amount of published patents referring to the way of avoiding the appearance of these impurities as far as possible, both to achieve a better yield from the main reaction of producing pentaerythritol, and to achieve a more efficient separation and obtain a purer product.

The synthesis of pentaerythritol involves the reaction of four moles of formaldehyde and one mole of acetaldehyde. The reaction takes place in two differentiated steps. The first at a pH of from 10 to 11 is an aldol condensation, in which three moles of formaldehyde and one mole of acetaldehyde are consumed, to give pentaerythritose.

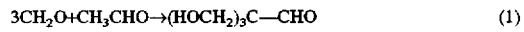

Thereafter, the aldehyde obtained in the aldol condensation is subjected to a crossed Cannizzaro reaction, at a pH of not less than 9, whereby one molecule of the pentraerythritose is reduced to pentaerythritol, and another of formaldehyde is oxidized to formic acid, which in the sodium hydroxide alkaline medium gives the sodium formate.

The temperatures at which these reactions are conducted are fundamental.

The Cannizzaro reaction is slow at low temperatures of 20°–30° C., while the aldol reaction is fast at these temperatures. Furthermore, the Cannizzaro reaction is dominant at 40°–60° C.. Therefore, the reaction mixture temperature should only be raised after all the acetaldehyde has been consumed. To achieve a greater extension of the aldolization reaction (1), an excess of formaldehyde is used in the solution.

This formaldehyde excess has special connotations. Under the influence of the alkali, it undergoes the Cannizzaro reaction to give methanol and sodium formate, whereby the solution pH drops and prevents the remaining reactants from adequately reacting. Or, if there is an excess of sodium hydroxide, autocondensations to give formoses are caused. Even worse, as said above, the excess or deficiency of formaldehyde affects the presence of higher or lower degree of formals of the various pentaerythritols formed and a smaller or larger proportion of these same pentaerythritols (di-, tri- and polipentaerythritol).

All these reactions depend on the temperature, pH and reaction time and on the concentration, amount and sequence in which the reactants are added, whereby compromise conditions allowing for high yields of pentaerythritol with the least possible amount of impurities have to be found.

British patent GB 958,654 explains the influence of the temperature and time of the different reactions, as well as of the excess formaldehyde used and describes a continuous process in several steps.

French patent FR 2,432,493 discloses a vertical reactor divided into various stages operating continuously wherein each stage is at a different temperature and with different molar proportions of sodium hydroxide, formaldehyde and acetaldehyde.

In other patents the use is disclosed of various reactors in series, such as for example German patent DE 1,910,057 which uses seven reactors in cascade and in each of which, variable amounts of acetaldehyde are added to an initial formaldehyde and sodium hydroxide solution. A similar system is used in document CS 261,843.

All these patents, which have improved the production yields of pentaerythritol over the earlier patents, disclose processes in which the reaction is conducted continuously, either in several reactors in cascade or in tubular reactors.

Continuous operation has its advantages, but also its drawbacks. Among the latter there may be cited the difficulty of getting the reactants to mix sufficiently quickly, and the subsequent cooling, since, otherwise, undesirable coloured products are formed as a result of the reaction being highly exothermal.

Furthermore, if several reactors are used, the process becomes more expensive and if the tubular reactor is used, it must be very long. Tubes 95 m long are disclosed in the patents (GB 958,654). This is so, because a certain dwell time is required in the reactor, together with a high liquid flowrate therein. To achieve the mixture as quickly as possible, the reactor diameter must be small and, therefore, it must have a substantial length and this makes temperature control in the various reactor portions difficult.

Other steps of the known processes are described in various publications. Thus, it is described that once the reaction has taken place in the continuous reactor or reactors, the resulting mixture is slightly acidified, either with acetic acid (U.S. Pat. No. 2,790,836, U.S. Pat. No.

2,978,514) or with formic acid (BE 626,804, DE 1,162,824). Thereafter, the excess formaldehyde is removed by steam entrainment distillation (U.S. Pat. No. 2,790,836, U.S. Pat. No. 2,978,514) and the resulting formaldehyde-free solution is evaporated under vacuum to a concentration such that the pentaerythritol precipitates in part, but not the sodium formate. Thereafter the precipitated pentaerythritol is separated from the rest of the solution, either by centrifugation or by filtration. After washing, the solid is formed by pentaerythritol, pentadierythritol and polypentaerythritols, linear formal (PMF), traces of sodium formate and other impurities and forms the so-called raw pentaerythritol. The filtered solution contains the sodium formate, the pentaerythritol which is soluble under the working conditions, the CMF and the remaining impurities or formoses. This solution is sent to the sodium formate recovery, either by crystallization, by cooling or by evaporation. The raw pentaerythritol is redissolved and subjected to high-temperature acid hydrolysis (U.S. Pat. No. 2,978,514), GB 799,182, GB 958,654) after which the resulting solution is purified by passing it through an activated carbon bed, decolouring it. The purified pentaerythritol solution is transferred to the evaporator-crystallizers where the solution is concentrated. The crystal suspension is filtered or centrifuged by known techniques.

Residual solutions are produced in each of the above described steps and beneficial use thereof is fundamental for obtaining an economically profitable yield.

On the other hand, the impurities produced in the reaction must be removed from the system through a liquid flow known as waste liquor.

Nevertheless, these processes have drawbacks, since the waste liquor is accompanied by a certain amount of valuable products which it is wanted to obtain (pentaerythritol and sodium formate), whereby the finished product yield is reduced if they are not recovered. The literature contains various patents studying recovery processes of these valuable products from the waste liquor (for example U.S. Pat. No. 4,083,931, U.S. Pat. No. 4,105,575, U.S. Pat. No. 4,277,620, U.S. Pat. No. 4,328,366). This recovery involves a number of additional operations for which equipment and reagents making the process more expensive are required. The excess waste liquor finally has to be subjected to a biological treatment to destroy the organic matter.

SUMMARY OF THE INVENTION

It is an aim of the invention to overcome the above mentioned drawbacks, and to reduce to a minimum the expense of the above treatments, to which end the proportion of waste liquor produced in the plant is reduced to the smallest possible amount. This is, as said above, one of the aims of the invention and is achieved basically by reducing the production of by-products during the reaction.

These aims are achieved by means of a process of the type described in the first paragraph of this description and which is characterized in that, in the first place, a formaldehyde solution and thereafter, simultaneously but separately, a sodium hydroxide solution and acetaldehyde are supplied, forming a reaction mixture and because the exit flow from the said buffer tank is substantially constant and continuous.

According to the invention, it has surprisingly been seen that if the NaOH is added gradually such that the pH of the reaction mixture of the aqueous formaldehyde solution and the acetaldehyde is held at all times between 10 and 11, the temperature varies with the elapsed time and the acetaldehyde flowrate also varies with the time, the amounts of secondary compounds of the reaction are reduced by 20 to 40% over the conventional processes.

In a preferred embodiment of the invention the flowrate of the said sodium hydroxide solution supply is subject at least to a variation and also the acetaldehyde supply flowrate is subject at least to a variation.

The variation of each of said flowrates may take place either substantially continuously or determine at least two periods of different flowrates, the flowrates being held substantially constant during each of said periods.

The invention also contemplates that the temperature at which the reactions are conducted be variable and that this variation be substantially continuous. This variability may be determined by at least two periods at different temperatures.

According to another feature of the invention, at the start of the reactions, the temperature is held in the range of 20° to 38° C., while at the end of the reactions the temperature is held in the range of 42° to 48° C.

Also according to the invention, the concentration of the formaldehyde solution is in the range of 20 to 30 wt %, the concentration of the sodium hydroxide solution is in the range of 12 to 20 wt % and the acetaldehyde is substantially pure. The molar proportions $CH_2O/NaOH/AcH$ are in the range of 5.1–9.5/1.05–1.4/1.0.

In a preferred embodiment of the invention, the successive supplies to the reactor comprise: a first period in which substantially half of the volumes is supplied, the temperature being held within the range of 22° to 28° C.; a second period in which substantially one fourth part of the volumes is supplied, the temperature being held within the range of 32° to 38° C., the duration of said second period being substantially the same as that of the first period; and a third period in which the supplies to the reactor are completed, the temperature being held within the range of 42° to 48° C., the duration of said third period being greater than that of the second period.

Once the reaction has ended, the resulting solution is acidified. Thereafter the volatile compounds, formaldehyde and methanol, are removed entrained by steam, the solution is concentrated by evaporation under vacuum and the first suspension obtained is filtered by known techniques.

The solid obtained, pentaerythritol, dipentaerythritol and formals, is dissolved in the mother liquors of the filtration of the solids obtained in the subsequent crystallizations of preparation of the pentaerythritol, a mixture of approximately 86–90% of monopentaerythritol and 10–14% of dipentaerythritol. This solution of pentaerythritol and formals is hydrolyzed in an acid medium according to conventional procedures and is then purified with activated carbon and suitably concentrated and crystallized.

Depending on the quality desired, the reaction is conducted in one way or another to obtain either a single quality of monopentaerythritol of 94–97.7% purity or two differentiated qualities, one of 98% monopentaerythritol and the other known as "technical penta" containing from 86–90% of monopentaerythritol and 10–14% of dipentaerythritol.

The sodium formate obtained simultaneously with the pentaerythritol in the reaction is produced by concentration and crystallization of the filtrate of the first suspension according to conventional procedures.

The invention also contemplates that the hydrolysis of the formals may be carried out prior to the concentration of the reaction solution.

Once the addition of reactants has ended, it is desirable to hold the mixture at a temperature of 45°±3° for a time, to make sure that the reaction is complete. Thereafter, it is acidified with formic acid at pH 5–6 to avoid subsequent undesirable reactions and is evacuated to a tank from which the process is carried out continuously.

Examples 1 and 2 are given below, corresponding to the process of the invention and Example 3 relating to a conventional process, allowing comparisons to be established.

EXAMPLE 1

To a reactor provided with stirring and a cooling system to hold the adequate temperature, there was added a 22% formaldehyde solution and then, separately but simultaneously, a 16% NaOH solution and the pure acetaldehyde, such that the pH was held always between 10–11. The flowrate was such that half of the reactants supply was effected in 25 minutes and the temperature was held at 25° C. Thereafter, the supply flowrate was varied so that half of the remaining supply was charged in a further 25 minutes, with the temperature being allowed to rise to 35° C. Finally, the remaining supply was added over 35 minutes and the temperature was controlled so as not to rise above 45° C. at the end of the reaction. The proportions of total $CH_2O/NaOH/AoH$ added had the molar ratio of 5.4/1.12/1. After the supply had terminated, the mixture was held for 10 minutes at 45° C. Thereafter, the mixture was acidified with formic acid to pH 5.5 and evacuated from the reactor to a buffer tank, from which the process became continuous, and was subjected to the processes of removal of volatile compounds, concentration, filtration, hydrolysis, purification and crystallization, according to known processes, as described hereinbefore.

Table 1 gives the initial concentrations of the formaldehyde and sodium hydroxide solutions, as well as the concentrations of monopentaerythritol, dipentaerythritol and impurities present in the reaction liquor at the end of the reaction. The two product qualities mentioned above, i.e. one 98% monopenta and the other 86–90% monopenta and 10–14% dipentaerythritol, were produced from that solution.

The amount of organic impurities from which it was not possible to recover pentaerythritol was 3.1% relative to the pentaerythritol obtained, which represents a 35% reduction over the conventional process.

EXAMPLE 2

To a reactor provided with stirring and a cooling system to hold the adequate temperature, there was added a 22% formaldehyde solution and then, separately but simultaneously, a 16% NaOH solution and the pure acetaldehyde, such that the pH was held always between 10–11. The flowrate is such that half of the reactants supply was effected in 25 minutes and the temperature was held at 25° C. Thereafter, the supply flowrate was varied so that half of the remaining supply was charged in a further 25 minutes, with the temperature being allowed to rise to 35° C. Finally, the remaining supply was added over 35 minutes and the temperature was controlled so as not to rise above 45° C. at the end of the reaction. The proportions of total $CH_2O/NaOH/AcH$ added had the molar ratio of 9.2/1.1/1. After the supply had terminated, the mixture was held for 10 minutes at 45° C. Thereafter, the mixture was acidified with formic acid to pH 5.5 and evacuated from the reactor to a buffer tank, from which the process became continuous, and was subjected to the processes of removal of volatile compounds, concentration, filtration, hydrolysis, purification and crystallization, according to known processes, as described hereinbefore.

Table 1 gives the initial concentrations of the formaldehyde and sodium hydroxide solutions, as well as the concentrations of monopentaerythritol, dipentaerythritol and impurities present in the reaction liquor at the end of the reaction. A single quality of pentaerythritol with a maximum of 2.3% of dipentaerythritol, was produced from this solution.

The amount of organic impurities from which it was not possible to recover pentaerythritol was 3.8% relative to the pentaerythritol obtained, which represents a 21% reduction over the conventional process.

EXAMPLE 3

To a reactor provided with stirring and a cooling system to hold the adequate temperature, there was added on the one hand a mixture of a 22% formaldehyde ($CH_2O$) solution and a 16% sodium hydroxide (NaOH) solution and on the other the pure acetaldehyde (AcH), in amounts such that the molar ratio $CH_2O/NaOH/AcH$ was 5.4/1.15/1. The acetaldehyde addition operation lasted 50 minutes and the heating/cooling was controlled such as to hold a maximum temperature of 46° C. After holding the mixture at this temperature for a further 10 minutes, it was acidified with formic acid to pH 5.5. The reactor mixture was sent to a buffer tank, from which the process became continuous, and was subjected to the processes of removal of volatile compounds, concentration, filtration, hydrolysis, purification and crystallization, according to known processes.

Table 1 gives the initial concentrations of the formaldehyde and sodium hydroxide solutions, as well as the concentrations of monopentaerythritol, dipentaerythritol and impurities present in the reaction liquor at the end of the reaction. Both product qualities i.e. one 98% monopenta and the other 86–90% monopenta and 10–14% dipentaerythritol, were produced from that solution.

The amount of organic impurities from which it was not possible to recover pentaerythritol was 4.8% relative to the pentaerythritol obtained.

TABLE 1

| PATENT YIELDS | | Ex. 1 | Ex. 2 | Ex. 3 |
| --- | --- | --- | --- | --- |
| Initial formaldehyde concentration | % | 22 | 22 | 22 |
| Initial sodium hydroxide concentration | % | 16 | 16 | 16 |
| Formaldehyde/acetaldehyde molar ratio | | 5.4 | 9.2 | 5.4 |
| Sodium hydroxide/acetaldehyde molar ratio | | 1.12 | 1.10 | 1.15 |
| Monopentaerythritol | % | 9.56 | 6.73 | 9.6 |
| Dipentaerythritol | % | 0.69 | 0.15 | 0.41 |
| DPE/MPE + DPE | | 6.7 | 2.2 | 4.1 |
| Impurities | % | 3.1 | 3.8 | 4.8 |
| Difference | | 1.7 | 1 | 0 |
| Yield relative to acetaldehyde | % | 80.3 | 79.7 | 78.8 |

What I claim is:

1. A process for the preparation of pentaerythritol, comprising the initial steps of: [a] reacting formaldehyde with acetaldehyde, to give pentaerythritose; and subsequent reaction of said pentaerythritose with formaldehyde and sodium hydroxide, to give a solution containing pentaerythritol; and [b] acidification of said pentaerythritol-containing solution with formic acid; said steps [a] and [b] being conducted in a reactor, with the supply of formaldehyde ($CH_2O$), sodium hydroxide (NaOH), acetaldehyde (AcH) and formic acid (HCOOH) and at the end of said steps the formed pentaerythritol-containing solution being drained to a buffer tank of a capacity greater than that of the reactor, new reactions and a new acidification operation being successively reinitiated in said reactor by fresh supplies, wherein, in the first place, a formaldehyde solution and thereafter, simultaneously but separately, sodium hydroxide solution and acetaldehyde are supplied, forming a reaction mixture and because the exit flow from the said buffer tank is substantially constant and continuous.

2. The process of claim 1, wherein the sodium hydroxide is added gradually such that the pH of said reaction mixture is held between 10 and 11, and throughout the addition the temperature and the acetaldehyde flowrate vary.

3. The process of claim 1, wherein at least one of the sodium hydroxide supply and acetaldehyde supply flowrates undergoes at least one variation.

4. The process of claim 3, wherein the variation of each of said flowrates takes place substantially continuously.

5. The process of claim 3, wherein the variation of each of said flowrates determines at least two periods of different flowrates, the flowrates being held substantially constant during each of said periods.

6. The process of claim 1, wherein said reactions are conducted at a variable temperature.

7. The process of claim 6, wherein said variability is substantially continuous.

8. The process of claim 6, wherein said variability determines at least two periods of different temperatures.

9. The process of claim 7, wherein at the start of said reactions the temperature is held within the range of 20° to 38° C., while at the end of said reactions the temperature is held within the range of 42° to 48° C.

10. The process of claim 1, wherein the concentration of said formaldehyde solution is in the range of 20 to 30 wt %, the concentration of said sodium hydroxide solution is in the range of 12 to 20 wt % and said acetaldehyde is substantially pure and the molar proportions $CH_2O/NaOH/AcH$ are in the range of 5.1–9.5/1.05–1.4/1.0.

11. The process of claim 1, wherein the successive supplies to said reactor comprise: a first period in which substantially half of the volumes is supplied, the temperature being held within the range of 22° to 28° C.; a second period in which substantially one fourth part of the volumes is supplied, the temperature being held within the range of 32° to 38° C., the duration of said second period being substantially the same as that of the first period; and a third period in which the supplies to the reactor are completed, the temperature being held within the range of 42° to 48°, the duration of said third period being greater than that of the second period.

* * * * *